United States Patent [19]

Hasson

[11] Patent Number: 4,489,732

[45] Date of Patent: Dec. 25, 1984

[54] GYNECOLOGICAL INSTRUMENT

[76] Inventor: Harrith M. Hasson, 2043 N. Sedgwick, Chicago, Ill. 60614

[21] Appl. No.: 420,404

[22] Filed: Sep. 20, 1982

[51] Int. Cl.³ .............................................. A61B 5/10
[52] U.S. Cl. .................................. 128/778; 33/174 D
[58] Field of Search ...................... 128/778; 33/174 D

[56] References Cited

U.S. PATENT DOCUMENTS

| | | | |
|---|---|---|---|
| 3,706,307 | 12/1972 | Hasson | 128/778 |
| 4,016,867 | 4/1977 | King et al. | 128/778 |
| 4,121,572 | 10/1978 | Krzeminski | 128/778 |
| 4,204,548 | 5/1980 | Kurz | 128/778 |
| 4,224,951 | 9/1980 | Hasson | 128/778 |
| 4,362,167 | 12/1982 | Nicolai et al. | 128/778 |

FOREIGN PATENT DOCUMENTS 44877 2/1982 European Pat. Off. ............ 128/778

*Primary Examiner*—Kyle L. Howell
*Assistant Examiner*—John C. Hanly
*Attorney, Agent, or Firm*—Wood, Dalton, Phillips, Mason & Rome

[57] ABSTRACT

A sound for uterine measurement including an elongated probe provided with expandable wings at one end. A button may be selectively moved to control the extension or collapse of the wings and a stop is reciprocally mounted on the probe and has a stop surface facing the wings which is adapted to engage the cervix. A coil spring surrounds the probe and biases the stop toward the distal end of the sound and a measuring scale is carried by the instrument. A moveable index point is provided and connected to the stop so as to cooperate with the scale depending upon relative positioning of the stop on the probe. A protective housing surrounds the spring for all positions of movement of the stop to prevent the spring from coming in contact with the tissue of a patient. Preferably, the protective housing is transparent and carries the scale with the index being movable within the housing.

5 Claims, 5 Drawing Figures

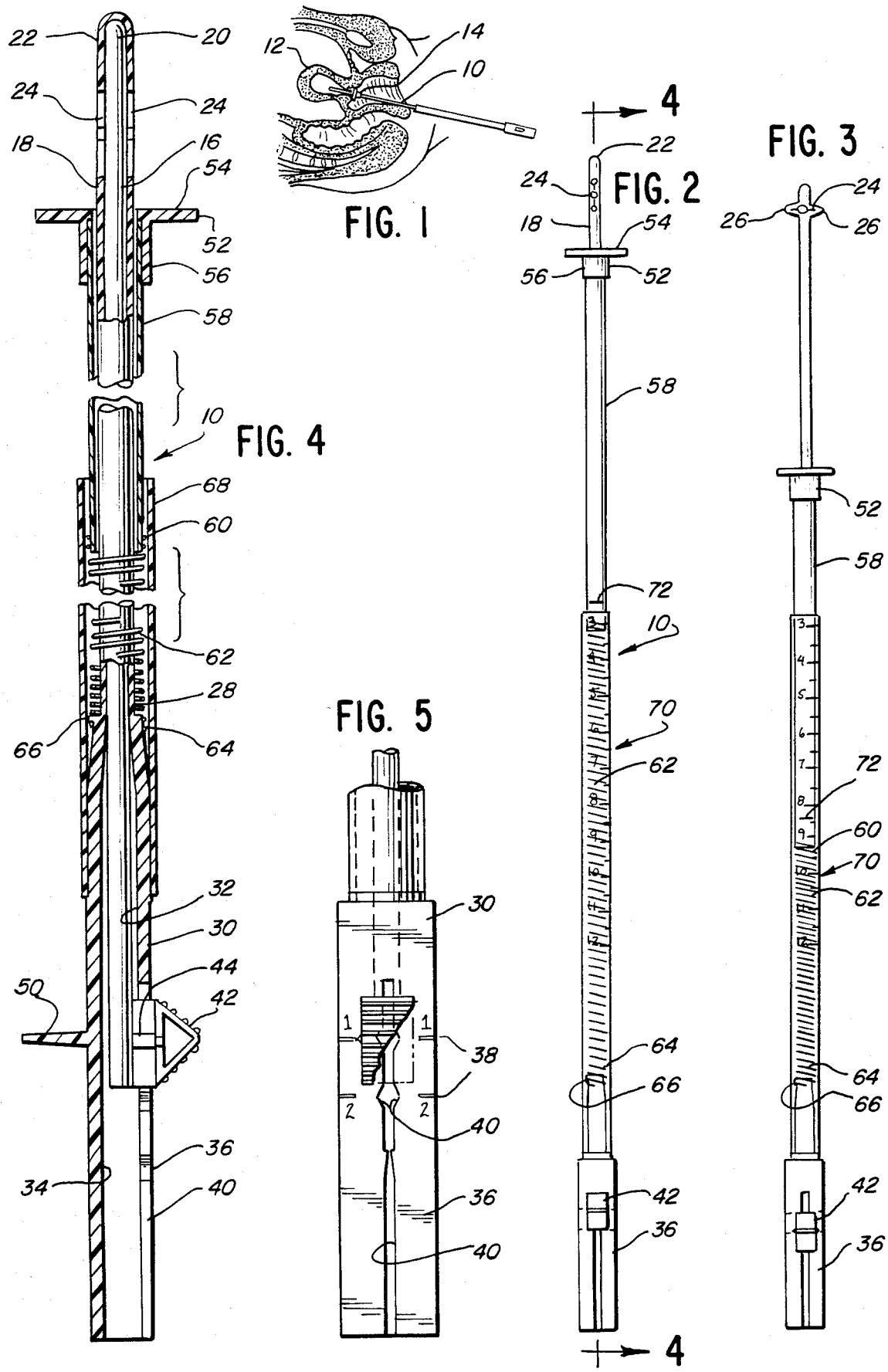

GYNECOLOGICAL INSTRUMENT

FIELD OF THE INVENTION

This invention relates to a gynecological instrument, and more specifically, an instrument useable in measuring anatomical features of the cervical canal, isthmus and uterus.

BACKGROUND ART

Prior art of possible relevance includes my prior U.S. Pat. No. 3,706,307 issued Dec. 19, 1972 and U.S. Pat. No. 4,016,867 issued Apr. 12, 1977 to King et al.

With the increasing awareness of the importance of endometrial cavity size to intrauterine device insertion and performance and of unique anatomical conditions which suggest individualization of medical management, there have evolved a number of proposals of measuring instruments as, for example, those disclosed in the previously identified United States patents. While such instruments have functioned satisfactorily for their intended purpose, room for improvement exists.

For example, in the instrument described in my prior U.S. Pat. No. 3,706,307, the measuring scale begins in close proximity to the distal end of the probe forming part of the instrument with the consequence that, in some instances, the scale may be wholly or partially obscured by the patient's body making it difficult to read. Furthermore, the stop employed in that instrument, in the form of the sleeve, must be manually positioned against the cervix by the physician using the instrument. Since the stop forms part of the measuring apparatus, if not properly placed, the dimensions of the uterus or cervical canal cannot be accurately determined.

King et al disclose a similar measuring instrument which avoid the forementioned problems. King et al spring bias the stop in the direction of the distal end of the probe such that the spring urges the stop against the cervix eliminating the need for manual placement of the stop by the physician. Furthermore, King et al locate the measuring scale at the proximal end of the probe where the likelihood that it will be obscured by a portion of the patient's body is eliminated entirely. However, in accomplishing these improvements, King et al have introduced a disadvantage in that the biasing spring employed in connection with the stop is a coil spring which is exposed on the probe, which may come in contact with the tissue of the patient during a measuring procedure and which may cause patient discomfort by reason of the collapsing of the convolutions of the coil spring upon one another while the probe is being inserted and after the stop has abutted the cervix.

The present invention is directed to overcoming one or more of the above problems.

SUMMARY OF THE INVENTION

According to the invention there is provided an instrument for determining anatomical characteristics of body cavities and passageways or the like which includes an elongated probe adapted to be inserted in a body cavity or passageway. Expandable means are disposed at one end of the probe and means are carried by the instrument for selectively controlling the expandable means. A stop is reciprocally mounted on the probe and has a stop surface facing the expandable means which is adapted to engage a body surface surrounding a body cavity, a body passageway or the like when the probe is inserted into such cavity or passageway. A coil spring surrounds the probe and biases the stop towards the expandable means. A measuring scale is carried by the instrument and a movable index cooperates with the scale. The index is connected to the stop for movement therewith. A protective housing surrounds the spring for all positions of movement of the stop.

In a preferred embodiment, the scale is on the housing.

In a highly preferred embodiment, the housing includes means for allowing visual access to the index means which is movable within the housing. The scale is disposed on the housing.

In the optimal embodiment, the housing is formed of transparent material so as to allow viewing of the index means through the housing itself.

Other objects and advantages will become apparent from the following specification taken in connection with the accompanying drawings.

DESCRIPTION OF THE DRAWINGS

FIG. 1 is a diagrammatic view of a gynecological instrument made according to the invention inserted within the uterus of a patient;

FIG. 2 is an elevational view of the instrument with the movable components thereof in one configuration.

FIG. 3 is a view similar to FIG. 2 but with the movable components of the instrument in another configuration;

FIG. 4 is a sectional view taken approximately along the line 4—4 in FIG. 2; and FIG. 5 is an expanded, fragmentary elevational view of the hand held end portion of the instrument.

DESCRIPTION OF THE PREFERRED EMBODIMENT

An exemplary embodiment of the gynecological instrument made according to the invention in its intended mode of use is illustrated in FIG. 1. The same includes an elongated probe 10 which may be inserted into the uterus 12 of a patient via the cervical canal. A movable stop 14 carried on the probe 10 abuts the entrance to the cervical canal and, by means to be described, is utilized in determining such dimensions as total uterine length, length of the cervical canal, and endometrial cavity length.

Referring now to FIGS. 2-5, the instrument will be described in greater detail. The probe 10 is formed of an internal, semi-rigid rod 16 reciprocally received within a sleeve of biologically inert plastic 18. The distal end 20 of the rod 16 is fixed by any suitable means to the distal end 22 of the sleeve 18 as, for example, by the means disclosed in my previously identified patent. Diametrically opposite from each other, and in close proximity to the distal end 22 of the sleeve 18 are axially elongated slits 24 in the sleeve 18. When the rod 16 is fully extended within the sleeve 18, the sleeve 18 will have the appearance illustrated in FIG. 2. Conversely, when the rod 16 is retracted within the sleeve 18, by reason of its distal end 20 being secured to the distal end 22 of the sleeve 18, the sleeve will separate at the slits 24 as illustrated in FIG. 3 to form two radially extending wings 26. If desired, reference may be made to my previously identified U.S. Patent for a further explanation of such structure.

Returning to FIG. 4, the proximal end 28 of the sleeve 18 terminates in a handle 30. The handle 30 has a hollow interior 32 which reciprocally receives the rod 16.

As best seen in FIG. 5, one side of the handle 30 has a flat indicator surface 36 provided with indicia 38 showing first and second positions. A slot 40 extends to the interior cavity 34 through the surface 36 and a button 42 secured to the rod 16 within the cavity 34 is movable within the slot 40 between the two positions designated by the indicia 38.

The button 42, within the slot 40, carries lateral projections 44 (only one of which is shown) which may be selectively received in detent recesses 46 associated with each of the positions designated by the indicia 38 to hold the button 42 in either such position. The handle 30 is made of a relatively rigid plastic that possesses sufficient resiliency so as to allow movement of the button 42 between the positions by yielding sufficiently to allow the projections 44 to move from one set of recesses 46 to the other within the slot 40.

Oppositely of the button 42 on the handle 30 is a finger grip 50. When the button 42 is to be moved from one position to another, the index finger may be placed about the finger grip 50 and the button 42 shifted with the thumb.

By reason of this construction, it will be appreciated that the rod 16 may be moved between the two positions to cause the distal end 22 of the sleeve 18 to assume either the configuration illustrated in FIG. 2 or the configuration shown in FIG. 3.

The instrument includes a stop in the form of a plastic disk 52 having a surface 54 facing the distal end 22 of the sleeve 18. The disk 52 includes an axial sleeve 56 which is fitted upon an elongated tube 58 reciprocally mounted on the probe. The end of the tube 58 opposite the disk 52 is secured to one end 60 of a coil spring 62 of the compression variety. The opposite end 64 of the coil spring is fitted over a small lip 66 on the handle 30 so as to be secured thereto.

As a result of this construction, it will be appreciated that the stop 52 is biased by the spring 62 toward the distal end 22 of the sleeve 18.

An elongated, cylindrical housing 68 is secured to the handle 30 by any suitable means and has sufficient axial length so as to extend about the spring 62 when the latter is unstressed. In other words, the housing 68 surrounds the spring 62 for all positions of movement of the stop 52.

In a highly preferred embodiment, the housing 68 is formed of transparent plastic and a numerical scale best illustrated in FIGS. 2 and 3 and given the general reference numeral 70 disposed thereon.

As can be seen from FIG. 4, the tube 58 is of lesser diameter than the housing 68 and is slidable along the sleeve 18 into the housing 68. The tube 58, at its end remote from the stop 52, carries an index point or marker 72 which cooperates with the scale 70 to provide desired measurements to the user of the instrument.

Applicability

The instrument is used as follows. The cervix is grasped with a suitable instrument such as a tenaculum and the distal end 22 of the sleeve 18 is introduced through the cervix into the endometrial cavity until the fundus of the uterus 12 is contacted. The position of the index 72 on the scale 70 is then read and indicates the total uterine length. This occurs as a result of the stop 52 encountering the cervix such that the index 72 moves relative to the remainder of the instrument as insertion continues.

At this point, the button 42 is moved from its first position to its second position to cause the proximal end 22 of the sleeve 18 to assume the configuration illustrated in FIG. 3, that is, with the wings extended.

The instrument is gently withdrawn until resistance is met indicating contact of the wings 26 with the cervicoisthmic region. Throughout this procedure, the spring 62 will be urging the stop 52 against the cervix with the result that a new reading will be obtained on the scale 70. The resulting measurement is an indication of the cervical length, i.e., length of the cervical canal, and a true measurement of such length is then obtained by subtracting a known figure equal to the combination of the distance between the proximal side of the wings to the tip or distal end of the sleeve 18, and the distance caused by retracting rod 16 within sleeve 18 to extend wings 26, in a typical construction, 1.3 centimeters.

The button 42 may then be moved back to its original position to collapse the wings 26 and the instrument withdrawn. To determine the endometrial cavity length, it is only necessary to subtract the measured length, as corrected, of the cervical canal from the total uterine length, both such measurements being obtained in the manner mentioned previously.

It will be observed that the scale 70 is disposed on the instrument at a location quite remote from the distal end 22 of the sleeve 18 such that the same will not be obscured by any part of the patient's body enabling the measurement to be easily and accurately read from the scale.

It will also be observed that there is no need for a physician to manually locate the stop 52, the stop 52 being automatically properly positioned by the bias of the spring 62. At the same time, it will be appreciated that the spring 62 is completely housed within the housing 68 at all times and therefore cannot come in contact with tissues of the patient such that the possibility of patient discomfort caused by contact of the collapsing coils during compression of the spring 62 with the tissue is completely avoided.

I claim:

1. An instrument for determining anatomical characteristics of body cavities and passageways or the like comprising
    an elongated hollow sleeve adapted to be inserted in a body cavity, passageway, or the like;
    expandable means at one end of said sleeve;
    a handle at the other end of said sleeve;
    an elongated rod slidably received within said sleeve and connected to said expandable means;
    means connected to said handle for selectively sliding said rod to operate said expandable means;
    a stop reciprocally mounted on said sleeve and having a stop surface facing said expandable means and adapted to engage a body surface surrounding a body cavity, passageway or the like when said sleeve is inserted thereinto;
    a coil spring mounted on the exterior of and surrounding said sleeve between said stop and said handle and biasing said stop toward said expandable means;
    a measuring scale mounted in fixed relation to said sleeve;
    index means for indicating movement of said stop in relation to said scale;

means for connecting said index means to said stop for movement therewith; and a protective housing extending from said handle about said sleeve and surrounding said spring for all positions of movement of said stop on said sleeve.

2. The instrument of claim 1 wherein said scale is on said housing.

3. The instrument of claim 1 wherein said housing is formed of transparent material and said scale is on said housing; and said protective housing surrounds said means for connecting in the region of said index means.

4. An instrument for determining anatomical characteristics of body cavities and passageways or the like comprising an elongated probe adapted to be inserted in a body cavity, passageway, or the like;

expandable means at one end of said probe;

means connected to said expandable means for selectively controlling said expandable means;

a stop slidably mounted on said probe and having a stop surface facing said expandable means and adapted to engage a body surface surrounding a body cavity, passageway or the like when said probe is inserted thereinto;

a coil spring on the exterior of and surrounding said probe and biasing said stop toward said expandable means;

a protective housing including a hollow cylinder of transparent material about said probe and surrounding said spring for all positions of movement of said stop on said probe and including a measuring scale extending along said probe;

index means for indicating the position of said stop in relation to said scale; and means positioned within said cylinder for connecting said index means to said stop for movement therewith.

5. The instrument of claim 4 wherein said housing surrounds said means for connecting in the region of said index means and said housing includes means for allowing visual access to said index means; said scale being disposed on said housing.

* * * * *